United States Patent
Miyata et al.

(10) Patent No.: US 7,825,080 B2
(45) Date of Patent: Nov. 2, 2010

(54) AQUEOUS SOLUTION OF OLANEXIDINE, METHOD OF PREPARING THE AQUEOUS SOLUTION, AND DISINFECTANT

(75) Inventors: Kazuyoshi Miyata, Itano-gun (JP); Yasuhide Inoue, Naruto (JP); Akifumi Hagi, Tokushima (JP); Motoya Kikuchi, Tokushima (JP); Hitoshi Ohno, Naruto (JP); Kinji Hashimoto, Naruto (JP); Kinue Ohguro, Tokushima (JP); Tetsuya Sato, Itano-gun (JP); Hidetsugu Tsubouchi, Tokushima (JP); Hiroshi Ishikawa, Otsu (JP); Takashi Okamura, Naruto (JP); Koushi Iwata, Naruto (JP)

(73) Assignees: Otsuka Pharmaceutical Co., Ltd., Tokyo (JP); Otsuka Pharmaceutical Factory, Inc., Tokushima (JP)

( * ) Notice: Subject to any disclaimer, the term of this patent is extended or adjusted under 35 U.S.C. 154(b) by 613 days.

(21) Appl. No.: 11/588,395

(22) Filed: Oct. 27, 2006

(65) Prior Publication Data

US 2007/0041866 A1   Feb. 22, 2007

Related U.S. Application Data

(62) Division of application No. 10/557,736, filed as application No. PCT/JP2004/007434 on May 25, 2004.

(30) Foreign Application Priority Data

May 28, 2003 (JP) .............................. 2003-150846

(51) Int. Cl.
C11D 7/26 (2006.01)
C11D 7/32 (2006.01)
C11D 7/50 (2006.01)

(52) U.S. Cl. ..................... 510/383; 510/488; 510/499; 510/506; 422/28

(58) Field of Classification Search ............... 510/383, 510/488, 499, 506; 422/28
See application file for complete search history.

(56) References Cited

U.S. PATENT DOCUMENTS 5,234,832 A    8/1993    Disch et al.
5,376,686 A    12/1994   Ishikawa et al.
5,478,864 A    12/1995   Nishihara et al.
5,977,034 A    11/1999   Walkinbarger, Jr.
5,997,759 A    12/1999   Trinh et al.
5,998,358 A    12/1999   Herdt et al.
6,121,327 A    9/2000    Tsuzuki et al.
6,183,807 B1   2/2001    Gutzmann et al.
6,323,171 B1*  11/2001   Fonsny et al. ............... 510/384

FOREIGN PATENT DOCUMENTS

| CN | 1065453 A | 10/1992 |
|---|---|---|
| EP | 0 507 317 A2 | 10/1992 |
| GB | 815 925 | 7/1959 |
| JP | 05-194361 A | 8/1993 |
| JP | 5-194631 | 8/1993 |
| JP | 5-331057 | 12/1993 |
| JP | 5-331058 | 12/1993 |
| JP | 7-82235 | 3/1995 |
| JP | 2000-273004 A | 10/2000 |

OTHER PUBLICATIONS

Supervised by Suzuki et al, pp. C-1225 to C-1229 (2001).
Edited by Japan Pharmaceutical Excipients Council, Iyakuhin Tenkabutsu Jiten, Kabushiki Kaisha Yakuji Nipposha, pp. 119-121, 126-129 (1994).
Umehara K. et al., "In Vitro Characterization of the Oxidative Cleavage of the Octyl Side Chain of Olanexidine, A Novel Antimcrobial Agent, in Dog Liver Microsomes", vol. 28, No. 12, 2000, pp. 1417-1424 (XP002451421).
European Search Report dated Oct. 9, 2007.
European Office Action dated Nov. 24, 2008.
Chinese Office Action dated Dec. 8, 2006.

* cited by examiner

*Primary Examiner*—Gregory R Del Cotto
(74) *Attorney, Agent, or Firm*—Sughrue Mion, PLLC

(57) ABSTRACT

The present invention provides a disinfectant that contains olanexidine in a concentration sufficient to exhibit an effective bactericidal effect, and that has hardly any side effects such as skin irritation. Specifically, the present invention provides a disinfectant containing an aqueous solution that contains olanexidine and at least an equimolar amount of gluconic acid, and substantially contains neither an acid other than gluconic acid nor a salt of the acid other than gluconic acid.

6 Claims, No Drawings

AQUEOUS SOLUTION OF OLANEXIDINE, METHOD OF PREPARING THE AQUEOUS SOLUTION, AND DISINFECTANT

CROSS-REFERENCE TO RELATED APPLICATIONS

This application is a Divisional of U.S. application Ser. No. 10/557,736, filed Mar. 9, 2006; which is a 371 of PCT/JP2004/007434, filed May 25, 2004; the entire disclosures of each of which are hereby incorporated herein by reference.

TECHNICAL FIELD

The present invention relates to an aqueous solution containing olanexidine, a method of preparing the aqueous solution, and a disinfectant containing the aqueous solution.

BACKGROUND ART

Olanexidine is a compound with high bactericidal activity having the chemical name 1-(3,4-dichlorobenzyl)-5-octylbiguanide. Research has been carried out into bactericides containing olanexidine hydrochloride as an active ingredient (see Japanese Patent No. 2662343, etc.).

Olanexidine has very poor solubility in water, and hitherto known salts of olanexidine are also poorly soluble in water. For example, the solubility at 0° C. of olanexidine hydrochloride in water has been measured to be less than 0.05% (W/V), and the solubility of free olanexidine is a further order of magnitude less than this. Consequently, sufficient bactericidal activity cannot be expected of an aqueous solution merely having olanexidine dissolved therein, and moreover, depending on the conditions the olanexidine may precipitate out.

In the case of making an aqueous preparation of olanexidine in particular, to make the concentration of the olanexidine sufficient for exhibiting effective bactericidal activity, and to reduce the possibility of the olanexidine precipitating out, it has thus been considered necessary to use a dissolution aid such as a surfactant.

DISCLOSURE OF THE INVENTION

It is an object of the present invention to provide an aqueous solution that contains olanexidine at a concentration sufficient to exhibit an effective bactericidal effect, and moreover is stable without allowing precipitation of olanexidine even at a high concentration, a preparation method thereof, and a disinfectant containing the aqueous solution (or a composition for disinfection).

The present inventors carried out extensive researches to attain the above object, and as a result succeeded in obtaining an olanexidine aqueous solution that contains olanexidine at a concentration of at least 0.1% (W/V). More specifically, the inventors neutralized or alkalized, for example, a suspension of an acid addition salt of olanexidine with an aqueous solution of an alkali to obtain olanexidine in the free form, washed the free olanexidine thoroughly with water to remove the acid that had formed the acid addition salt of olanexidine and the alkali salt of the acid, and then added the free olanexidine to an aqueous gluconic acid solution. The aqueous solution thus obtained was a stable solution containing olanexidine at a concentration incomparably higher than the concentration attained by dissolving free olanexidine or a salt of olanexidine with an acid other than gluconic acid in water. With such an aqueous solution, it was no longer essential to use a surfactant. Based on these findings, the present inventors carried out further researches and accomplished the present invention.

Note that in Japanese Patent No. 2662343, various acids are listed as acids that form acid addition salts with monobiguanide derivatives, and gluconic acid is included among them. However, in Japanese Patent No. 2662343, there is no specific mention of a gluconic acid salt of olanexidine, and no such a salt is isolated, and moreover there is no disclosure of a solution of such a salt. Furthermore, there is no suggestion regarding the solubility of such a salt in water.

Specifically, the present invention relates to the following aqueous solutions, preparation methods thereof, disinfectants (or compositions for disinfection), etc.

(1) An aqueous solution containing olanexidine and at least an equimolar amount of gluconic acid, and substantially containing neither an acid(s) other than gluconic acid nor a salt(s) of the acid(s) (i.e., the acid(s) other than gluconic acid).

(2) The aqueous solution according to (1) above, wherein the concentration of olanexidine is 0.1 to 20% (W/V).

(3) The aqueous solution according to (2) above, wherein the concentration of olanexidine is 10 to 20% (W/V).

(4) A method of preparing the aqueous solution according to any one of (1) through (3) above, comprising neutralizing or alkalizing an aqueous suspension of an acid addition salt of olanexidine with an aqueous solution of an alkali to precipitate a solid, washing the precipitated solid with water, and then dissolving the washed solid in a gluconic acid aqueous solution.

(5) The method according to (4) above, wherein the neutralization or alkalization is carried out at a temperature of 20 to 30° C.

(6) A disinfectant containing the aqueous solution according to any one of (1) through (3) above.

(7) The disinfectant according to (6) above, wherein the disinfectant is an aqueous preparation.

(8) The disinfectant according to (7) above, wherein the concentration of olanexidine is 0.001 to 20% (W/V).

(9) The disinfectant according to (6) above, wherein the disinfectant is an alcoholic preparation.

(10) The disinfectant according to (9) above, wherein the concentration of olanexidine is 0.001 to 6% (W/V).

(11) The disinfectant according to any one of (6) through (10) above, which further contains a polyalkylene glycol.

(12) The disinfectant according to (11) above, wherein the concentration of the polyalkylene glycol is 0.5 to 10% (W/V).

(13) The disinfectant according to (11) or (12) above, wherein the polyalkylene glycol is a polyethylene-polypropylene glycol or a polyethylene glycol.

(14) An aqueous solution containing olanexidine at a concentration of at least 0.1% (W/V).

(15) Use of gluconic acid for solubilizing olanexidine in water.

(16) A method of disinfecting or sterilizing an object, comprising contacting the object with an effective amount of the disinfectant according to any one of (6) through (13) above.

(17) Use of a disinfectant according to any one of (6) through (13) above for disinfection or sterilization.

In the specification and claims, the concentration of each ingredient in an aqueous solution or disinfectant is, unless otherwise indicated, expressed as a weight per volume percentage "% (W/V)", i.e., the weight (g) of each ingredient/100 mL of the aqueous solution or disinfectant. When the disinfectant is an alcoholic preparation, the concentration of alcohol in the disinfectant is expressed as a volume per volume percentage "% (V/V)", i.e., the volume (mL) of alcohol/100 mL of the disinfectant.

Moreover, in the specification and claims, the concentration of olanexidine means the concentration of olanexidine in terms of the free form in an aqueous solution or in a disinfectant, which is determined by measuring the amount of free olanexidine in the aqueous solution or disinfectant by high-performance liquid chromatography.

DETAILED DESCRIPTION OF THE INVENTION

Aqueous Solution

The present invention provides an aqueous solution containing olanexidine at a concentration of at least approximately 0.1% (W/V) in terms of free olanexidine. The aqueous solution of the invention contains at least approximately 0.1% (W/V) olanexidine, and therefore can be used in the manufacture of various forms of disinfectants in accordance with the objective, including disinfectants that are diluted at the time of use. Moreover even in the case of preparing a disinfectant having a relatively high olanexidine concentration from the aqueous solution of the invention, there is no longer any risk of the olanexidine precipitating out in the obtained disinfectant. It is preferable that the olanexidine concentration in the aqueous solution be about 0.1 to 20% (W/V). As described above, by solubilizing olanexidine, which is poorly soluble in water, the aqueous solution of the present invention has an outstanding advantage such that for the first time it can be stably used in various forms of pharmaceutical preparations such as liquids and ointments.

Olanexidine is a compound having the chemical name 1-(3,4-dichlorobenzyl)-5-octylbiguanide represented by the following formula (1).

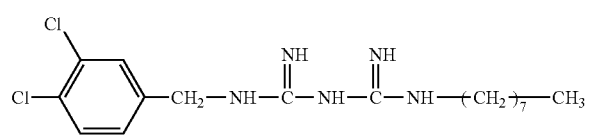

(1)

An example of a preferable means for dissolving olanexidine in water at a concentration of at least about 0.1% (W/V) is to make at least an equimolar amount of gluconic acid, preferably 1 mole to a slight excess of gluconic acid per mole of the olanexidine, coexist with the olanexidine. In such an aqueous solution containing olanexidine and at least an equimolar amount of gluconic acid, the olanexidine and the gluconic acid may form a salt, or the two may exist in the free form, or the gluconic acid salt of olanexidine may coexist with free olanexidine and free gluconic acid.

Furthermore, it is preferable that the aqueous solution containing olanexidine and gluconic acid substantially contain neither an acid other than gluconic acid nor a salt of the acid (i.e., the acid other than gluconic acid). More specifically, it is preferable that the concentration of any acid other than gluconic acid and an salt of the acid (i.e., the acid other than gluconic acid) in the aqueous solution be not more than approximately 0.05% (W/V). Here "acid other than gluconic acid" means a substance other than gluconic acid that provides hydrogen ions in an aqueous solution. Examples of "salt of the acid other than gluconic acid" include base addition salt of the acid, such as a salt with an inorganic base, e.g., an alkali metal salt such as a sodium salt or a potassium salt, an alkaline earth metal salt such as a calcium salt or a magnesium salt, an aluminium salt, or an ammonium salt; a salt with an organic base such as trimethylamine, triethylamine, pyridine, picoline, ethanolamine, diethanolamine, triethanolamine, dicylohexylamine or N,N-dibenzylethylenediamine; and so on.

Preparation Method of the Aqueous Solution

Described below is a preferable method of preparing an aqueous solution that contains olanexidine and gluconic acid, and substantially contain neither an acid other than gluconic acid nor a salt of the acid (i.e., the acid other than gluconic acid).

Olanexidine is generally obtained as a crystalline acid addition salt such as a hydrochloride. Therefore, the acid addition salt such as olanexidine hydrochloride is first suspended in water, and an alkali such as a sodium hydroxide or a potassium hydroxide is then added to the suspension in the form of the alkali itself or in the form of an aqueous alkaline solution to precipitate free olanexidine. The amount of an alkali to be added is such that free olanexidine can be precipitated, i.e., such that the suspension is neutral or alkaline. For example, the amount may be at least an equivalent relative to the acid forming the acid addition salt of olanexidine.

After the alkali addition, the mixture is stirred for about 1 to 5 hours at about 0° C. to room temperature, preferably about 20 to 30° C., and more preferably at a temperature in the vicinity of 25° C. In the present invention, the alkali may be an inorganic base or an organic base such as those previously mentioned.

Next, the free olanexidine solid precipitated by the above treatment is filtered off, and is washed with water to remove the acid that formed the olanexidine acid addition salt and a salt of the acid and the alkali. After washing with water, the solid is resuspended in a solvent such as water, is again filtered off, and is rewashed with water, and it is preferable to repeat this procedure once or several times. Additionally, if desired, free olanexidine of high purity can be obtained by dissolving the solid in a solvent such as an alcohol, and adding water to the solution to precipitate crystals of free olanexidine. If the acid that formed the acid addition salt of the olanexidine and a salt of the acid and the alkali substantially remain, then the olanexidine in the aqueous solution may return to the poorly soluble original salt.

Specifically, the residual amount of the acid that formed the olanexidine acid addition salt and a salt of the acid and the alkali in the aqueous solution of the invention is preferably not more than about 0.05% (W/V). For example, in the case of neutralizing or alkalizing a suspension of olanexidine hydrochloride with an aqueous sodium hydroxide solution, it is preferable that the residual sodium chloride concentration in the aqueous solution be not more than about 0.05% (W/V).

Next, the solid obtained above is added to an aqueous gluconic acid solution, or an aqueous gluconic acid solution is added to the solid, and the mixture is stirred, whereby the aqueous solution of the invention can be obtained. This operation can be carried out at room temperature, but heating may be carried out as required. The concentration of the aqueous gluconic acid solution used can be suitably selected so long as the aqueous solution contains at least an equimolar amount, specifically, about 1 to 1.1 moles of gluconic acid per mole of free olanexidine to be added thereto.

The aqueous gluconic acid solution used in this step can be prepared by dissolving gluconic acid itself, or can be prepared using a gluconic acid precursor that changes into gluconic acid in an aqueous solution such as gluconolactone. As described earlier, if any acid other than gluconic acid or a salt of the acid (i.e., the acid other than gluconic acid) is present, then the olanexidine in the aqueous solution of the present invention may form a poorly soluble acid addition salt, and hence when preparing the aqueous gluconic acid solution, it is desirable to remove beforehand anions (e.g. chloride ions, bromide ions etc.) that are produced from acids other than gluconic acid and that may form a salt, and salts of such anions with cations (such as sodium ions, potassium ions etc.). in the aqueous solution, such that such ions and salts substantially do not remain in the aqueous gluconic acid solution. As described earlier, the preferable extent of the removal is such that acids other than gluconic acid and salts of such acids remain in the aqueous solution at a concentration of not more than about 0.05% (W/V).

The above procedure gives an aqueous solution containing olanexidine and gluconic acid, and substantially containing neither an acid other than gluconic acid nor a salt of the acid. The aqueous solution obtained remains in a clear transparent state at room temperature for a long time even if the olanexidine concentration is approximately 20% (W/V) in terms of free olanexidine.

Disinfectant

The olanexidine aqueous solution of the present invention described above contains at least about 0.1% (W/V) olanexidine, and thus exhibits effective disinfectant and bactericidal action, and hence is useful as a disinfectant. For example, the olanexidine aqueous solution of the present invention described above can be used as a disinfectant as such.

Alternatively, the olanexidine aqueous solution can be made into an aqueous preparation by diluting it with purified water, or, for example, can be made into an alcoholic preparation by diluting with an alcohol such as ethanol, isopropanol, or with denatured alcohol, and if necessary with a purified water.

Moreover, the olanexidine aqueous solution can be made more viscous using a thickener or the like and can thus be made into a viscous disinfectant. Alternatively, ethanol for disinfection or the like can be added to the olanexidine aqueous solution, thus making the olanexidine aqueous solution into a quick-drying disinfectant that can be expected to have both a quick-acting bactericidal effect due to the ethanol, and a sustained effect due to the olanexidine.

Furthermore, the olanexidine aqueous solution of the present invention can be used not only in the form of liquid preparations as described above but also in disinfectants in other suitable forms. Examples of forms other than liquid preparations include ointments, creams, gels, foams, aerosols, scrubs and so on. These forms can be prepared by using commonly used suitable carriers.

The olanexidine concentration in the disinfectant of the present invention is preferably adjusted to be 0.001 to 20% (W/V) in terms of free olanexidine.

When the disinfectant of the present invention is an alcoholic preparation obtained by diluting it with an alcohol or denatured alcohol, the bactericidal effect of the alcohol (specifically, ethanol, isopropanol, etc.) can be expected as well, and hence the concentration of the olanexidine can be reduced. When the disinfectant of the present invention is an alcoholic preparation, the olanexidine concentration in the disinfectant is preferably about 0.001 to 6% (W/V). In this case, the alcohol concentration in the disinfectant is preferably about the same as that of ethanol for disinfection, i.e. about 70 to 85% (V/V).

If desired, a polyalkylene glycol can be further added to the disinfectant of the present invention. Addition of a polyalkylene glycol to the disinfectant of the present invention produces the surprising effect of further reducing skin irritation without decreasing the bactericidal activity.

Specific examples of the polyalkylene glycol include polyethylene-polypropylene glycols and polyethylene glycols. The type thereof (molecular weight, polymerization degree of ethylene oxide, polymerization degree of propylene oxide, etc.) can be suitably selected from commonly used types in accordance with the form and application of the disinfectant and so on.

For example, preferable polyethylene-polypropylene glycols are those having a polymerization degree of ethylene oxide (EO) of about 10 to 300 (especially, about 15 to 200), and a polymerization degree of propylene oxide (PO) of about 10 to 100 (especially, about 15 to 70). Preferable polyethylene glycols are those having a molecular weight of 200 to 10000.

A particularly preferable polyalkylene glycol is a polyethylene-polypropylene glycol with a polymerization degree of EO of about 15 to 200 and a polymerization degree of PO of about 15 to 70.

The amount of the polyalkylene glycol added can be suitably selected in accordance with the form and application of the disinfectant, the concentration of olanexidine and so on. Generally, the polyalkylene glycol, if used, may be used at a concentration of about 0.01 to 50% (W/V) in the disinfectant, and preferably about 0.5 to 20% (W/V).

If desired, additives commonly used in preparations such as ordinary liquid preparations, ointments and the like can be suitably added to the disinfectant of the present invention insofar as it does not adversely affect the dissolution of olanexidine in water. Examples of such additives include preservatives, moisturizers, thickeners, nonionic surfactants other than polyalkylene glycols, cationic surfactants, antioxidants, perfumes, colorants and so on, and also include other bactericidal disinfectants and medicinal agents, etc. Note, however, that it is desirable to avoid the additives that are likely to form a poorly soluble acid addition salt with olanexidine, such as acids other than gluconic acid and salts of such acids, in particular citric acid, phosphoric acid, and salts thereof, etc.

Examples of the preservatives include p-oxybenzoic acid esters such as methyl p-oxybenzoate, ethyl p-oxybenzoate and propyl p-oxybenzoate, and chlorhexidine gluconate.

Examples of the moisturizers include polyhydric alcohols such as propylene glycol, 1,3-butanediol, polyethylene glycol and glycerol; synthetic macromolecular compounds such as carboxymethylcellulose and hydroxypropylcellulose; natural macromolecular compounds such as pectin, chitosan, chitin and xanthan gum; polysaccharides such as sorbitol, mannitol and xylitol; and fatty acid esters such as glycerol triisooctanoate, isopropyl palmitate, isopropyl myristate and olive oil.

Examples of the thickeners include water-soluble polymers such as carboxyvinyl polymers, cellulosic water-soluble macromolecular compounds, povidones and polyvinyl alcohols. Carboxyvinyl polymers are macromolecular compounds obtained by polymerizing carboxylic acids such as acrylic acid or methacrylic acid, and generally, one having a molecular weight of about 1,000,000 to 3,000,000 is used. Examples of cellulosic water-soluble macromolecular compounds include methylcellulose, ethylcellulose, hydroxyethylcellulose, hydroxypropylcellulose, carboxymethylcellulose and hydroxypropylmethylcellulose.

Examples of the nonionic surfactants other than polyalkylene glycols include lauric acid diethanolamide, coconut oil fatty acid diethanolamide, coconut oil fatty acid monoethanolamide, lauric acid monoisopropanolamide, oleic acid monoisopropanolamide, palm kernel oil fatty acid diethanolamide, and polyoxyethylene coconut oil fatty acid monoethanolamide.

Examples of such cationic surfactants include a lauryl dimethyl amine oxide and alkyl dimethyl amine oxides, etc.

Examples of other bactericidal disinfectants that can be mixed with the disinfectant of the present invention include surfactant bactericidal disinfectants, and phenolic bactericidal disinfectants.

Examples of other medicaments that can be blended into the disinfectant of the present invention include local anesthetics, vasoconstrictors, adrenocortical hormones, antihistamines, astringents, antipruritics, analgesics/antiphlogistics, anti-trichophyton agents, sulfa drugs, keratolytics, and vitamins.

The disinfectant of the present invention has a broad antibacterial spectrum for various microbes. For example, the disinfectant has an effective bactericidal and disinfectant action on gram-positive bacteria such as *Staphylococci, Streptococci, Enterococci,* and *Listeria* and *Propionibacterium* spp; and gram-negative bacteria such as *Escherichia coli, Shigella, Salmonella, Citrobacter, Klebsiella, Enterobacter, Serratia, Proteus, Morganella, Yersinia, Vibrio, Pseudomonas, Acinetobacter, Neisseria, Haemophilus,* and *Bacteroides* spp.

The disinfectant also has an antiviral action for virus such as Influenza virus with envelope, Human immunodeficiency virus, Herpes simplex virus, and Vesicular stomatitis virus, and has antifungal action on yeast-like fungi such as *Candida* spp, *Cryptococcus neoformans*, and *Saccharomyces cerevisiae*.

The disinfectant of the present invention means an agent that can be widely used for the purpose of killing, decreasing, or controlling etc. various microbes such as those described above.

The disinfectant of the present invention exhibits bactericidal and disinfectant activities by contacting an object containing the microbes with an effective amount of the disinfectant. Contacting methods are not particularly limited, and specific examples thereof include immersion, spraying, bed bathing etc. Examples of the object include skin and/or hands of a human or animal, medical equipment, lavatories, bathrooms, furniture, articles and so on.

Therefore, the disinfectant of the present invention can be suitably used for disinfecting skin/hands, skin subjected to surgery, skin wounded, medical equipment, operating rooms, sickrooms, furniture, equipment and other articles, etc.

Moreover, the aqueous solution or disinfectant of the present invention may be used by impregnating it in a base fabric. Examples of such base fabrics include cotton wool, gauze, paper, non-woven cloths, towels, other cloths and so on. Usable such base fabrics may be water-decomposable or non-water-decomposable.

Effects of the Invention

The aqueous solution of the present invention has a broad antibacterial spectrum, and exhibits a rapidly appearing and a long-lasting bactericidal activity. Furthermore, the aqueous solution is very stable even at high olanexidine concentration, and can thus be stored for a long time. Moreover, the aqueous solution is excellent in terms of safety because of its low irritative and toxic properties. In addition, the aqueous solution has no problems with color, odor or taste, and can thus easily be made into preparations.

Furthermore, the aqueous solution also has the advantage of being noncorrosive, and hence can be widely used for disinfecting metallic medical equipment, etc.

Best Mode for Carrying out the Invention

Following is a description of preferable examples, preparation examples and test examples of the present invention; however the present invention is not limited to these examples.

Note that in the examples, "%" means "% (W/V)" unless otherwise stated.

The olanexidine concentration of each sample is measured using high-performance liquid chromatography under the following conditions.

Column: stainless steel tube with an internal diameter of 4.6 mm and a length of 15 cm filled with TSK gel Octyl-80Ts (manufactured by Tosoh corporation)

Temperature: 40° C.

Solvent: a mixture of acetonitrile and 0.05 v/v % phosphoric acid solution containing 10 mM sodium lauryl sulfate (volume ratio of 13:7).

Detection method: absorbance at 237 nm was measured with an ultraviolet absorption detector.

Example 1

Preparation of an Aqueous Solution

Aqueous Solution 1

20.9 g (50 mmol) of olanexidine hydrochloride hemihydrate was added to 250 mL of a 1 N aqueous sodium hydroxide solution, and the suspension was stirred for 1.5 hours at room temperature (25° C.). The solid was filtered off, and washed with water. The solid obtained was further suspended in 250 mL of purified water, the suspension was stirred for 5 minutes at room temperature, and the solid was filtered off, and washed with water. This operation was carried out once more to remove sodium chloride formed. The solid obtained (free olanexidine) was put into purified water in which 8.9 g (50 mmol) of gluconolactone had been dissolved, and the mixture was stirred at room temperature until the solid dissolved, and then purified water was further added to give a total volume of 300 mL. The concentration of olanexidine in the aqueous solution obtained was measured by using high performance liquid chromatography to be 6% in terms of free olanexidine.

This aqueous solution was still transparent and colorless even after being left for several months at room temperature.

Example 2

Aqueous Solution 2

62.7 g (150 mmol) of olanexidine hydrochloride hemihydrate was added to 750 mL of a 1 N aqueous sodium hydroxide solution, and the suspension was stirred for 1.5 hours at room temperature (25° C.). The solid was filtered off and washed with water. The solid obtained was further suspended in 750 mL of purified water, the suspension was stirred for 5 minutes at room temperature, and the solid was filtered off, and washed with water. This operation was carried out once more to remove sodium chloride formed. The solid obtained (free olanexidine) was put into purified water in which 26.7 g (150 mmol) of gluconolactone had been dissolved, and the mixture was stirred at room temperature until the solid dissolved, and then purified water was further added to give a total volume of 300 mL. The concentration of olanexidine in the aqueous solution obtained was measured by using high performance liquid chromatography to be 18% in terms of free olanexidine.

This aqueous solution was still transparent and colorless even after being left for several months at room temperature.

Example 3

Aqueous Solution 3

69.8 g (167 mmol) of olanexidine hydrochloride hemihydrate was added to 830 mL of a 1 N aqueous sodium hydroxide solution, and the suspension was stirred for 1.5 hours at room temperature (25° C.). The solid was filtered off, and washed with water. The solid obtained was further suspended in 830 mL of purified water, the suspension was stirred for 5 minutes at room temperature, and the solid was filtered off, and washed with water. This operation was carried out once more to remove sodium chloride formed. The solid obtained (free olanexidine) was put into purified water in which 29.7 g (167 mmol) of gluconolactone had been dissolved, and the mixture was stirred at room temperature until the solid dissolved, and then purified water was further added to give a total volume of 300 mL. The concentration of olanexidine in the aqueous solution obtained was measured by using high performance liquid chromatography to be 20% in terms of free olanexidine.

This aqueous solution was still transparent and colorless even after being left for several months at room temperature.

Preparation Example 1

20 mL of Aqueous Solution 1 obtained in Example 1 was diluted with purified water to give a total volume of 240 mL. The solution was filled into polyethylene bottles, and then high-pressure steam sterilization was carried out, thus obtaining a disinfectant containing 0.5% olanexidine.

Preparation Example 2

Absolute ethanol (purity 99.5%, the same hereinafter) was added to 60 mL of Aqueous Solution 1 obtained in Example 1, and the mixture was uniformly mixed. Absolute ethanol was added thereto to give a total volume of 240 mL. The solution was filled aseptically into polyethylene bottles, thus obtaining a disinfectant containing 1.5% olanexidine.

Preparation Example 3

160 mL of absolute ethanol and 2 g of hydroxypropylcellulose were added to 10 mL of Aqueous Solution 1 obtained in Example 1, and the mixture was uniformly mixed. Purified water was added thereto to give a total volume of 200 mL. The solution was filled aseptically into polyethylene bottles, thus obtaining a viscous disinfectant containing 0.3% olanexidine.

Preparation Example 4

4.8 g of a polyethylene-polypropylene glycol (polymerization degree of ethylene oxide (EO): 160; polymerization degree of propylene oxide (PO): 30) was added to 20 mL of Aqueous Solution 1 obtained in Example 1, and purified water was added thereto to carry out dissolution and to give a final volume of 240 mL. The solution was filled into polyethylene bottles, and then high-pressure steam sterilization was carried out, thus obtaining a disinfectant containing 0.5% olanexidine.

Preparation Example 5

2.4 g of a polyethylene-polypropylene glycol (polymerization degree of EO: 196; polymerization degree of PO: 67) was added to 20 mL of Aqueous Solution 1 obtained in Example 1, and purified water was added thereto to carry out dissolution and to give a final volume of 240 mL. The solution was filled into polyethylene bottles, and then high-pressure steam sterilization was carried out, thus obtaining a disinfectant containing 0.5% olanexidine.

Preparation Example 6

19.2 g of polyethylene glycol 4000 was added to 20 mL of Aqueous Solution 1 obtained in Example 1, and purified water was added thereto to carry out dissolution and to give a final volume of 240 mL. The solution was filled into polyethylene bottles, and then high-pressure steam sterilization was carried out, thus obtaining a disinfectant containing 0.5% olanexidine.

Preparation Example 7

4.8 g of a polyethylene-polypropylene glycol (polymerization degree of EO: 160; polymerization degree of PO: 30) was added to 60 mL of Aqueous Solution 1 obtained in Example 1, and absolute ethanol was added thereto and uniformly mixed therewith so as to give a final volume of 240 mL. The solution was filled aseptically into polyethylene bottles, thus obtaining a disinfectant containing 1.5% olanexidine.

Preparation Example 8

160 mL of absolute ethanol, 2 g of hydroxypropylcellulose and 4.0 g of a polyethylene-polypropylene glycol (polymerization degree of EO: 160; polymerization degree of PO: 30) were added to 10 mL of Aqueous Solution 1 obtained in Example 1, and the mixture was uniformly mixed. Purified water was added thereto to give a final volume of 200 mL. The solution was filled aseptically into polyethylene bottles, thus obtaining viscous disinfectants containing 0.3% olanexidine.

Preparation Example 9

9.0 g of a polyethylene-polypropylene glycol (polymerization degree of EO: 160; polymerization degree of PO: 30) was added to 100 mL of Aqueous Solution 2 obtained in Example 2, and purified water was added thereto to carry out dissolution and to give a final volume of 180 mL. The solution was filled into polyethylene bottles, and then high-pressure steam sterilization was carried out, thus obtaining a disinfectant containing 10% olanexidine.

Preparation Example 10

1.2 g of a polyethylene-polypropylene glycol (polymerization degree of EO: 20; polymerization degree of PO: 20) was added to 20 mL of Aqueous Solution 1 obtained in Example 1, and purified water was added thereto to carry out dissolution and to give a final volume of 240 mL. The solution was filled into polyethylene bottles, and then high-pressure steam sterilization was carried out, thus obtaining a disinfectant containing 0.5% olanexidine.

Preparation Example 11

240 mL of absolute ethanol, 15.0 g of glycerol, 15.0 g of glycerol triisooctanoate and 0.6 g of a polyethylene-polypropylene glycol (polymerization degree of EO: 20; polymerization degree of PO: 20) were added to 10 mL of Aqueous Solution 1 obtained in Example 1, and the mixture was uniformly mixed, and then purified water was added thereto to give a final volume of 300 mL. The solution was filled aseptically into polyethylene bottles, thus obtaining a quick-drying rub-in-type hand disinfectant containing 0.2% olanexidine.

Preparation Example 12

6.3 g of a partially hydrolyzed polyvinyl alcohol, 1.8 g of lauric acid diethanolamide and 3.6 g of a polyethylene-polypropylene glycol (polymerization degree of EO: 20; polymerization degree of PO: 20) were added to 20 mL of Aqueous Solution 2 obtained in Example 2, and the mixture was uniformly mixed, adjusted to pH 4 to 7 by adding gluconic acid, and purified water was added thereto to give a final volume of 180 mL. The solution was filled into polyethylene bottles, and high-pressure steam sterilization was carried out, thus obtaining a disinfectant containing 2% olanexidine having the form of a scrub.

Preparation Example 13

40 g of a polyethylene-polypropylene glycol (polymerization degree of EO: 20; polymerization degree of PO: 20) was added to 160 mL of Aqueous Solution 3 obtained in Example 3, and the solution was filled into polyethylene bottles, and then high-pressure steam sterilization was carried out, thus obtaining a disinfectant containing 16% olanexidine intended for dilution at the time of use.

Preparation Example 14

0.9 g of a polyethylene-polypropylene glycol (polymerization degree of EO: 20; polymerization degree of PO: 20) was added to 5 mL of Aqueous Solution 2 obtained in Example 2, and the mixture was mixed uniformly, and purified water was added thereto to give a final volume of 90 L. The solution was filled aseptically into polyethylene bottles, thus obtaining a disinfectant containing 0.001% olanexidine.

Test Examples

Skin Irritation Test

The hair on the back of rabbits was shorn off, and rabbits having no island skin or wounds were selected. Each test preparation was openly applied to the rabbits once a day for four days. The second and subsequent applications of the test preparation were carried out after wiping the site of application with a cotton wool pad containing water. Evaluation was carried out once per day with regard to erythema and edema, and the total number of points for erythema and edema was taken as the evaluation score carried out in accordance with the following judgment criteria:

TABLE 1

Draize method judgement criteria

| Skin reaction judgment criteria | Erythema | No erythema | 0 |
| --- | --- | --- | --- |
| | | Very slight erythema | 1 |
| | | Clear erythema | 2 |
| | | Medium to severe erythema | 3 |
| | | Severe erythema (deep red color) to slight crust formation | 4 |
| | Edema | No edema | 0 |
| | | Very slight edema | 1 |
| | | Clear edema | 2 |
| | | Medium edema (approximately 1 mm) | 3 |
| | | Severe edema (more than 1 mm, spreads to surroundings) | 4 |

The results are shown in Table 2 as mean values (n=6).

TABLE 2

| Test Preparation | Day 1 (applied) | Day 2 (applied) | Day 3 (applied) | Day 4 (applied) | Day 5 | Day 6 | Day 7 | Day 8 |
| --- | --- | --- | --- | --- | --- | --- | --- | --- |
| Preparation Example 4 | 0 | 0 | 0 | 0 | 0 | 0 | 0 | 0 |
| Preparation Example 5 | 0 | 0 | 0 | 0 | 0 | 0 | 0 | 0 |
| Preparation Example 6 | 0 | 0.2 | 0.2 | 0.2 | 0 | 0 | 0.2 | 0.2 |
| Preparation Example 10 | 0 | 0 | 0 | 0 | 0 | 0 | 0 | 0 |
| Preparation Example 14 | 0 | 0 | 0 | 0 | 0 | 0 | 0 | 0 |

As is clear from the results, the disinfectants of the present invention have essentially no problem with regard to skin irritation, and that in particular the disinfectants of Preparation Examples 4, 5, 10 and 14, to which a polyethylene-polypropylene glycol had been added, were excellent in terms of skin irritation.

Moreover, the disinfectants of Preparation Examples 1 to 14 exhibited bactericidal action corresponding to the concentration of olanexidine, regardless of whether a polyalkylene glycol had been added thereto.

Reference Example 1

Preparation of Free Olanexidine

A 4 N aqueous sodium hydroxide solution (120 mL) was added to a suspension of olanexidine hydrochloride (40 g) in water (360 mL), and the mixture was stirred for 90 minutes at 25° C. The crystals obtained were filtered off by suction filtration, washed with water (500 mL), and then resuspended in water (500 mL). The suspension was stirred for 5 minutes at room temperature (approximately 25° C.), and the crystals were filtered off by suction filtration, and then washed with water (500 mL). This operation (washing) was repeated once more. The crystals obtained (wet weight: 127 g) were dissolved in methanol (200 mL), and then water (60 mL) was added. The resulting emulsion was left for 12 hours at room temperature, and then the crystals precipitated were filtered off by suction filtration. The crystals were dried under reduced pressure at room temperature, whereby free olanexidine (32 g) was obtained.

Reference Example 2

Preparation of a D$_2$O Solution Containing 3% Olanexidine Gluconate

The free olanexidine obtained in Reference Example 1 (40 mg) was suspended in D$_2$O (1 mL), a solution of gluconolactone (19.2 mg) in heavy water (1 mL) was added dropwise to the suspension, and the mixture was stirred for 24 hours at room temperature, thus preparing a D$_2$O solution containing olanexidine gluconate.

$^1$H-NMR (D$_2$O) δ (ppm): 0.75 (3H, t, J=7.1 Hz), 0.8-1.2 (12H, m), 2.6-2.8 (2H, m), 3.4-3.7 (4H, m), 3.9-4.0 (2H, m), 4.07 (2H, br s), 6.90 (1H, d, J=7.9 Hz), 7.09 (1H, d, J=7.9 Hz), 7.13 (1H, s)

INDUSTRIAL APPLICABILITY

The aqueous solution of the present invention has a broad antibacterial spectrum, and a rapidly appearing and long-lasting bactericidal activity. Therefore, the aqueous solution of the present invention is useful as a medical disinfectant.

The invention claimed is:

1. A method of disinfecting or sterilizing an object, comprising contacting the object with an effective amount of a disinfectant containing an aqueous solution containing 1-(3,4-dichlorobenzyl)-5-octylbiguanide,
   at least an equimolar amount of gluconic acid,
   a polyalkylene glycol selected from the group consisting of polyethylene-polypropylene glycol and polyethylene glycol, and
   wherein the concentration of an acid other than gluconic acid and a salt of the acid other than gluconic acid is not more than approximately 0.05% (W/V), wherein the concentration of 1-(3,4-dichlorobenzyl)-5-octylbiguanide is 0.1 to 20% (W/V), and the concentration of the polyalkylene glycol is 0.01 to 10% (W/V).

2. The method according to claim 1, wherein the disinfectant is an aqueous preparation.

3. The method according to claim 1, wherein the disinfectant is an alcoholic preparation.

4. The method according to claim 3, wherein the concentration of 1-(3,4-dichlorobenzyl)-5-octylbiguanide is 0.1 to 6% (W/V).

5. The method according to claim 1, wherein the polyalkylene glycol is a polyethylene-polypropylene glycol.

6. The method according to claim 5, wherein the polyalkylene glycol is a polyethylene-polypropylene glycol having a polymerization degree of ethylene oxide of about 10 to 300, and a polymerization degree of propylene oxide of about 10 to 100.

* * * * *